(12) United States Patent  
Hoffman et al.

(10) Patent No.: US 10,159,419 B2  
(45) Date of Patent: Dec. 25, 2018

(54) OPTICAL STIMULATION DEVICE

(71) Applicant: IMEC, Leuven (BE)

(72) Inventors: Luis Diego Leon Hoffman, Leuven (BE); Dries Braeken, Overpelt (BE); Silke Musa, Leuven (BE)

(73) Assignees: IMEC, Leuven (BE); KATHOLIEKE UNIVERSITEIT LEUVEN, KU LEUVEN R&D, Leuven (BE)

( * ) Notice: Subject to any disclaimer, the term of this patent is extended or adjusted under 35 U.S.C. 154(b) by 706 days.

(21) Appl. No.: 14/289,876

(22) Filed: May 29, 2014

(65) Prior Publication Data

US 2014/0356892 A1 Dec. 4, 2014

(30) Foreign Application Priority Data

May 29, 2013 (EP) .................................. 13169700

(51) Int. Cl.
| | |
|---|---|
| *A61N 5/06* | (2006.01) |
| *A61N 1/05* | (2006.01) |
| *A61B 5/04* | (2006.01) |
| *G01N 33/50* | (2006.01) |
| *A61B 5/00* | (2006.01) |

(52) U.S. Cl.
CPC ........ *A61B 5/04001* (2013.01); *A61B 5/4064* (2013.01); *A61N 5/0601* (2013.01); *A61N 5/0622* (2013.01); *G01N 33/5091* (2013.01); *A61B 5/40* (2013.01); *A61B 5/6868* (2013.01); *A61B 2562/164* (2013.01); *A61B 2562/166* (2013.01); *A61N 1/0529* (2013.01); *A61N 1/0551* (2013.01); *A61N 2005/0632* (2013.01); *A61N 2005/0643* (2013.01)

(58) Field of Classification Search
None
See application file for complete search history.

(56) References Cited

U.S. PATENT DOCUMENTS

| | | | | |
|---|---|---|---|---|
| 5,281,301 A | * | 1/1994 | Basavanhally | G02B 6/32 156/182 |
| 5,337,391 A | * | 8/1994 | Lebby | G02B 6/1221 385/88 |
| 6,469,785 B1 | * | 10/2002 | Duveneck | G01N 21/648 356/244 |
| 7,146,221 B2 | * | 12/2006 | Krulevitch | A61N 1/0543 607/116 |
| 7,869,853 B1 | * | 1/2011 | Say | A61M 5/1723 600/347 |
| 7,959,656 B2 | * | 6/2011 | Myeong | A61N 5/0613 606/10 |

(Continued)

*Primary Examiner* — Carl H Layno  
*Assistant Examiner* — Manolis Pahakis  
(74) *Attorney, Agent, or Firm* — McDonnell Boehnen Hulbert & Berghoff LLP

(57) ABSTRACT

In an aspect of the disclosure, a stimulation device includes a probe attached to a first support. The probe includes at least one grating coupler for coupling light into the probe. The device further includes at least one optical source for providing an optical stimulation signal mounted on a second support, and at least one means for detachably attaching the first support to the second support. The position of the at least one optical source is aligned with the position of the at least one grating coupler to allow light emitted from the at least one optical source to be received by the at least one grating coupler.

16 Claims, 10 Drawing Sheets

(56) References Cited

U.S. PATENT DOCUMENTS

| | | | | |
|---|---|---|---|---|
| 8,012,189 B1* | 9/2011 | Webb | A61N 5/0603 | 607/88 |
| 8,160,696 B2* | 4/2012 | Bendett | A61N 1/36014 | 607/3 |
| 8,465,425 B2* | 6/2013 | Heller | A61B 5/14532 | 600/365 |
| 8,469,610 B2* | 6/2013 | Shao | G02B 6/4292 | 385/76 |
| 8,498,699 B2* | 7/2013 | Wells | A61N 1/36017 | 607/3 |
| 8,688,188 B2* | 4/2014 | Heller | A61B 5/14532 | 600/345 |
| 9,066,695 B2* | 6/2015 | Say | A61B 5/14532 | |
| 9,248,269 B2* | 2/2016 | Kipke | A61B 5/04001 | |
| 9,700,736 B2* | 7/2017 | Seymour | A61N 5/0622 | |
| 2003/0233138 A1* | 12/2003 | Spooner | A61B 18/203 | 607/93 |
| 2004/0248318 A1* | 12/2004 | Weinberger | B01L 3/502715 | 436/173 |
| 2005/0253273 A1* | 11/2005 | Tai | B81C 1/0023 | 257/774 |
| 2006/0149342 A1* | 7/2006 | Huang | A61N 5/0603 | 607/88 |
| 2006/0217787 A1* | 9/2006 | Olson | A61N 5/0616 | 607/88 |
| 2006/0293727 A1* | 12/2006 | Spooner | A61N 5/0616 | 607/88 |
| 2008/0131834 A1* | 6/2008 | Shepherd | A46B 9/04 | 433/29 |
| 2008/0172113 A1* | 7/2008 | Gourgouliatos | A61N 5/0617 | 607/90 |
| 2008/0208283 A1* | 8/2008 | Vetter | A61N 1/0534 | 607/45 |
| 2008/0306576 A1* | 12/2008 | Boyden | A61N 5/0618 | 607/91 |
| 2009/0325424 A1* | 12/2009 | Aarts | A61B 5/0478 | 439/676 |
| 2010/0006784 A1* | 1/2010 | Mack | G02B 6/34 | 250/551 |
| 2010/0082019 A1* | 4/2010 | Neev | A61B 18/203 | 606/9 |
| 2010/0292758 A1* | 11/2010 | Lee | A61N 5/0601 | 607/55 |
| 2010/0324631 A1* | 12/2010 | Tass | A61M 21/02 | 607/88 |
| 2011/0024771 A1* | 2/2011 | Hajj-Hassan | B82Y 15/00 | 257/84 |
| 2011/0112591 A1* | 5/2011 | Seymour | A61B 5/0084 | 607/3 |
| 2011/0135252 A1* | 6/2011 | Kim | G02B 6/262 | 385/49 |
| 2011/0152976 A1* | 6/2011 | Perkins | A61N 5/0601 | 607/89 |
| 2011/0224554 A1* | 9/2011 | Vukeljic | G02B 6/3882 | 600/478 |
| 2011/0295347 A1* | 12/2011 | Wells | A61N 1/36032 | 607/89 |
| 2012/0089205 A1* | 4/2012 | Boyden | A61N 5/0601 | 607/88 |
| 2012/0123508 A1* | 5/2012 | Wentz | A61N 1/3787 | 607/88 |
| 2012/0287420 A1* | 11/2012 | McLaughlin | A61B 5/0084 | 356/72 |
| 2013/0023967 A1* | 1/2013 | Stafford | A61N 5/0622 | 607/89 |
| 2013/0030274 A1* | 1/2013 | Jamieson | A61B 5/6848 | 600/377 |
| 2013/0046148 A1* | 2/2013 | Tathireddy | A61B 5/04001 | 600/300 |
| 2013/0085398 A1* | 4/2013 | Roukes | A61B 5/0084 | 600/478 |
| 2013/0137955 A1* | 5/2013 | Kong | A61B 5/04 | 600/373 |
| 2013/0209026 A1* | 8/2013 | Doany | G02B 6/4214 | 385/14 |
| 2014/0277296 A1* | 9/2014 | Tolosa | A61N 5/0601 | 607/90 |
| 2016/0367836 A1* | 12/2016 | Kampasi | A61N 5/0622 | |

* cited by examiner

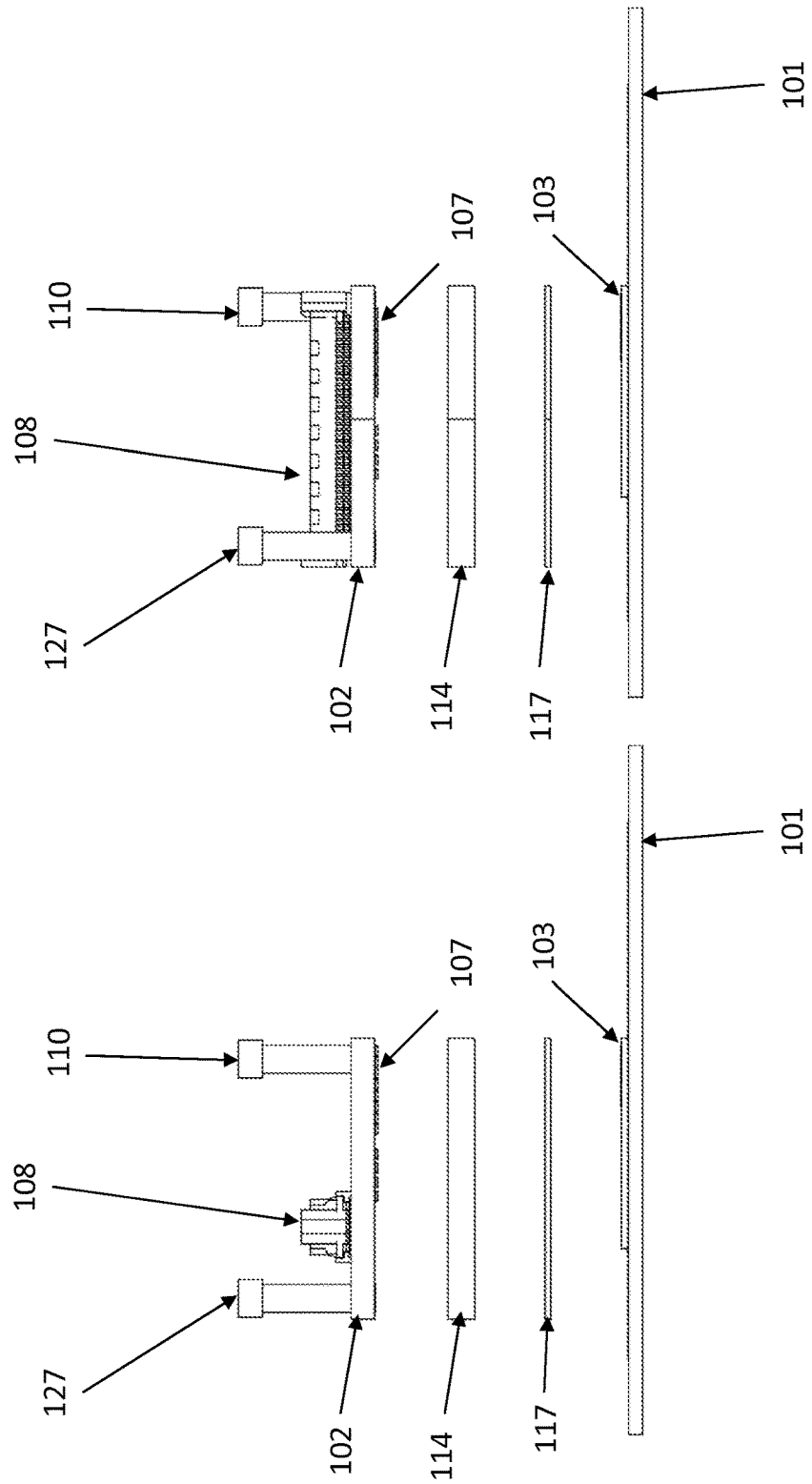

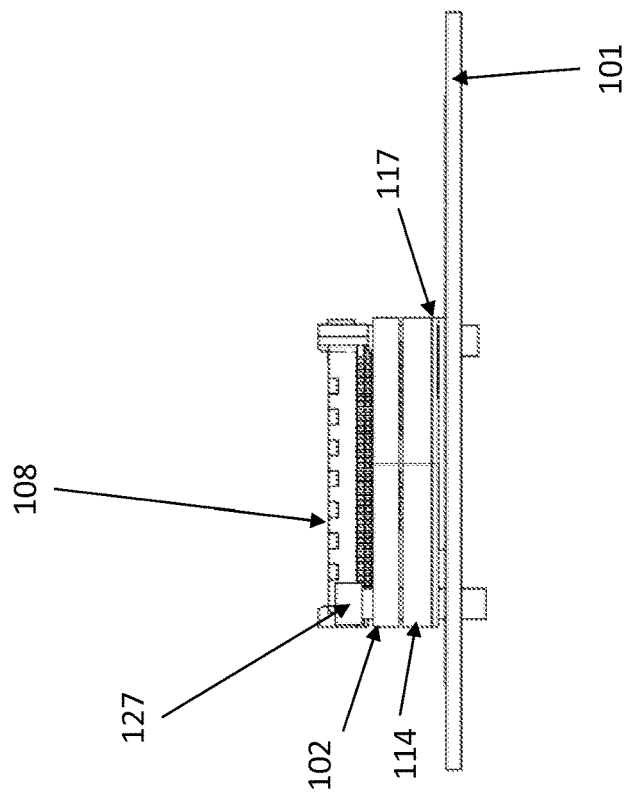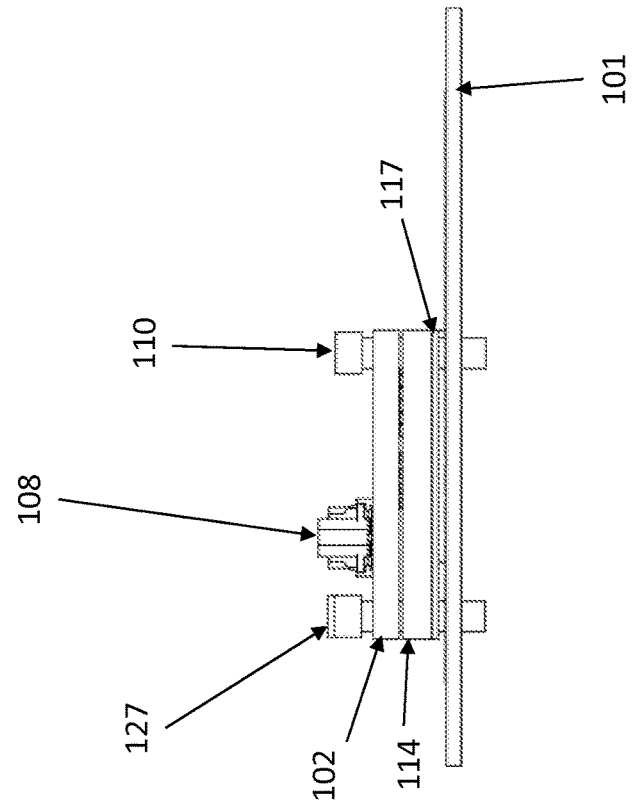

OPTICAL STIMULATION DEVICE

CROSS-REFERENCE TO RELATED APPLICATION

This application claims priority to European Patent Application No. 13169700.5 filed on May 29, 2013, the contents of which are hereby incorporated by reference

FIELD OF THE DISCLOSURE

The disclosure is related to devices for the stimulation of cells. In particular, the disclosure is related to compact and reusable devices for the optical stimulation of biological cells such as nervous tissue. The disclosure is also related to in-vivo and in-vitro devices for such purposes.

BACKGROUND TO THE DISCLOSURE

Optical stimulation of neurons in the brain based on optogenetic targeting of specific neurons is the next big thing in neuroscience. The technique makes it possible to stimulate specific neurons by light of a certain wavelength. Different stimulation devices are on the market today. However, these devices have some limitations.

A first group of state of the art stimulation devices uses probes with optical stimulation sites located on the probes, optically connected to optical fibers. These probes are inserted in the brain and the optical stimulation sites are used to stimulate particular areas of the brain. To couple light into the probe, optical fibers are attached to the probe. The use of optical fibers may pose problems as they can be bulky. A first problem is the compactness of the device, which is reduced due to the attachment of optical fibers to a probe. The problem increases when multiple optical fibers are connected to the probe to stimulate nervous tissue with light of multiple wavelengths. A second problem is the connectivity between the probe and the optical fiber. It requires a special connection in order to couple light efficiently in the probe (e.g., the angle in which the light enters the probe needs to be correct). Thus, specific, bulky connectors are necessary which increase the size and the cost of the device.

A second group of state of the art stimulation devices uses probes with optical sources positioned on the probes. The light of the optical source is coupled into the probes to stimulate specific regions of the brain. The problem with these devices is undesired heating, which is generated by the optical source. As the optical sources are positioned on the probes, the neurprobes tend to heat up. As a result, nervous tissue near the probe tends to heat up, resulting in tissue damage and unwanted side effects.

A different issue that arises with current state of the art optical neural stimulation devices is the reusability factor. Current optical probes are usually used only once and cannot be reused. After stimulation, the probe is disposed.

There is a need for stimulation devices that can overcome at least one of the drawbacks mentioned above.

SUMMARY OF THE DISCLOSURE

In a first aspect of the disclosure, a stimulation device includes a probe attached to a first support. The probe includes at least one grating coupler for coupling light into the probe. The device further includes at least one optical source for providing an optical stimulation signal mounted on a second support, and at least one means for detachably attaching the first support to the second support. The position of the at least one optical source is aligned with the position of the at least one grating coupler to allow light emitted from the at least one optical source to be received by the at least one grating coupler. The at least one means for detachably attaching the first support to the second support allows the first support to be detached from the second support. As a potential advantage, the second support may be reused, e.g., in combination with another first support.

According to an embodiment of the disclosure, the probe further includes a tip, a shaft comprising at least one electrode, and at least one optical stimulation site that is optically connected to the at least one grating coupler. The at least one grating coupler may be mounted on a head that is mounted on the first support, and the head further may include at least one bondpad electrically connected to the at least one electrode. While only the head of the probe is mounted to the first support, the shaft of the probe may be inserted in the human body or brain while the rest of the device remains outside of the body. As a potential advantage, this allows the device to be used as an in-vivo device.

According to an embodiment of the disclosure, the probe includes a silicon substrate, an interconnection layer, at least one electrode electrically connected to at least one bondpad via the interconnection layer, and at least one optical stimulation site optically connected to the at least one grating coupler via the interconnection layer. The device allows cells or tissue to be placed on top of the probe for stimulation or recording purposes. As a potential advantage, the device may be used as an in-vitro device.

According to an embodiment of the disclosure, the first support further comprises an electrical connector that is electrically connected to at least one bondpad of the probe. The electrical connector allows the probe to be connected to another device for read-out of electrical signals from the probe.

According to an embodiment of the disclosure, the second support further comprises an optical connector electrically connected to the at least one optical source for powering and/or controlling the at least one optical source. The optical connector allows the at least one optical source to be connected to an external device for controlling the at least one optical source. As a possible advantage, the device is compact as no optical fibers need to be attached to the device.

According to an embodiment of the disclosure, the at least one means for detachably attaching the first support to the second support includes a bolt and a nut.

According to an embodiment of the disclosure, the first or the second support further comprises at least one guiding means for aligning the position of the at least one grating coupler with the position of the at least one optical source. The at least one guiding means is used to align the first support with the second support to align the position of the at least one grating coupler with the position of the at least one optical source. As a potential advantage, light emitted by the at least one optical source is not diffused before reaching the at least one grating coupler.

According to an embodiment of the disclosure, the device further comprises an interface fitting located in between the first support and the second support. The interface fitting may include at least one through-hole aligned on one side of the interface fitting with one of the at least one grating coupler, and on the other side of the interface fitting with one of the at least one optical source. The interface fitting is used to align grating couplers with optical sources on a one-toone basis to avoid cross-illumination between optical sources. As a possible advantage, multiple optical sources may be used.

According to an embodiment of the disclosure, the interface fitting features a cut-out for providing space for bond wires on the first support. The cut-out provides space, e.g., for bond wires that may present on the first support. As a potential advantage, the first support may be attached to the second support in a very compact manner.

According to an embodiment of the disclosure, the device further comprises a gasket fitting located in between the first support and the second support. The gasket fitting may include at least one through-hole aligned on one side of the gasket fitting with one of the at least one grating coupler, and on the other side of the gasket fitting with one of the at least one optical source. The gasket fitting can help to ensure a perfect fitting between the interface fitting and the second support.

According to an embodiment of the disclosure, the probe is glued to the first support.

According to an embodiment of the disclosure, the first support and/or the second support and/or the interface fitting are printed circuit boards.

According to an embodiment of the disclosure, the gasket fitting is fabricated from an elastic material. Due to the elastic material, the gasket fitting is flexible. As a possible advantage, a perfect and tight fitting between the interface fitting and the second support is possible.

According to an embodiment of the disclosure, the at least one optical source is a LED.

The stimulation device may be used as a bio-probe, a neuroprobe, and/or a biosensor.

The stimulation device may be used for the stimulation of biological cells such as neurons in the brain, biological cells in the body.

BRIEF DESCRIPTION OF THE DRAWINGS

FIG. 8a illustrates a 2D backside view of a de-assembled embodiment of the disclosure using a micro-chip.

FIG. 8b illustrates a 2D frontside view of a de-assembled embodiment of the disclosure using a micro-chip.

FIG. 9a illustrates a 2D backside view of an assembled embodiment of the disclosure using a micro-chip.

FIG. 9b illustrates a 2D frontside view of an assembled embodiment of the disclosure using a micro-chip.

DETAILED DESCRIPTION OF THE DISCLOSURE

Figure 1:
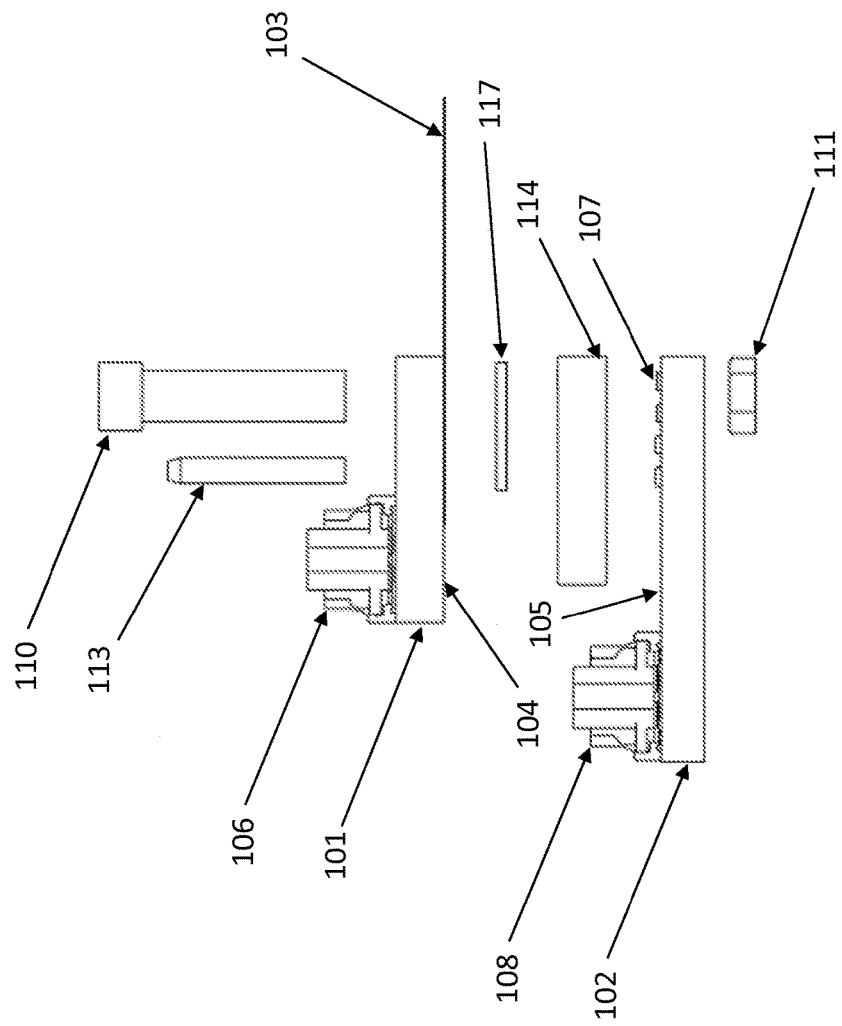
FIG. 1 illustrates a 2D side view of a de-assembled embodiment of the disclosure using a neuroprobe.

Where in embodiments of the present disclosure reference is made to "a PCB", this is defined generally as a printed circuit board. A printed circuit board may be used to mechanically support and electrically connect electronic components using conductive pathways, tracks or signal traces etched from, e.g., copper sheets laminated onto a non-conductive substrate.

Where in embodiments of the present disclosure reference is made to "a bondpad", this is generally defined as an electrically conductive, e.g., metallized, area on a surface of a semiconductor device to which connections can be made.

Where in embodiments of the present disclosure reference is made to "wire bonding", this is generally defined as a technique for making interconnections between an integrated circuit (IC) and a printed circuit board (PCB) during semiconductor device fabrication. The interconnection itself can be defined as "a bond wire". Wire bonding can also be used to make an electrical connection between two nodes on a PCB.

Where in embodiments of the present disclosure reference is made to "a probe", this is generally defined as a device to stimulate biological cells.

Where in embodiments of the present disclosure reference is made to "a bio-probe", this is generally defined as a probe that may be inserted in the body for the stimulation of organ tissue, for example. Such a bio-probe may be used to relieve pain, for example. The bio-probe may be an electrical or an optical stimulation device or a combination thereof.

Where in embodiments of the present disclosure reference is made to "a neuroprobe", this is generally defined as a probe that may be inserted in the brain for the stimulation of nervous tissue. Such a neuroprobe may be also used to record data from neurons in the brain. The neuroprobe may be an electrical or an optical stimulation device or a combination thereof.

Where in embodiments of the present disclosure reference is made to "a post", this is generally defined as a piece fixed firmly in an upright position that may be used as a stay or support.

The device presented in this disclosure may be used to optically stimulate biological cells. The device may be used to stimulate nervous tissue in the brain or cells in the body. The device may also be used to record electrochemical activity from biological cells such as neurons in the brain after or during optical stimulation.

In a first aspect of the disclosure, a stimulation device 100 is presented including a probe 103 attached to a first support 101. The probe 103 includes at least one grating coupler 121 for coupling light into the probe 103. The device 100 also includes at least one optical source 107 for providing an optical stimulation signal mounted on a second support 102, and at least one means for detachably attaching the first support 101 to the second support 102. In this aspect, the position of the at least one optical source 107 is aligned with the position of the at least one grating coupler 121 to allow light emitted from the at least one optical source 107 to be received by the at least one grating coupler 121.

According to an embodiment of the disclosure, the probe may be a bio-probe, a neuroprobe (e.g., a silicon neuroprobe), or a biosensor.

FIGS. 1, 2, 3, 4 illustrate different views of an embodiment of the disclosure:

FIG. 1 illustrates a side-view of an embodiment of a de-assembled stimulation device 100. Illustrated are: an electrical connector 106 and a probe 103 located on a first support 101; an optical connector 108 and optical sources 107 located on a second support 102; an interface fitting 114; a gasket fitting 117; a bolt 110; a nut 111; and a guiding post 113.

Figure 2:
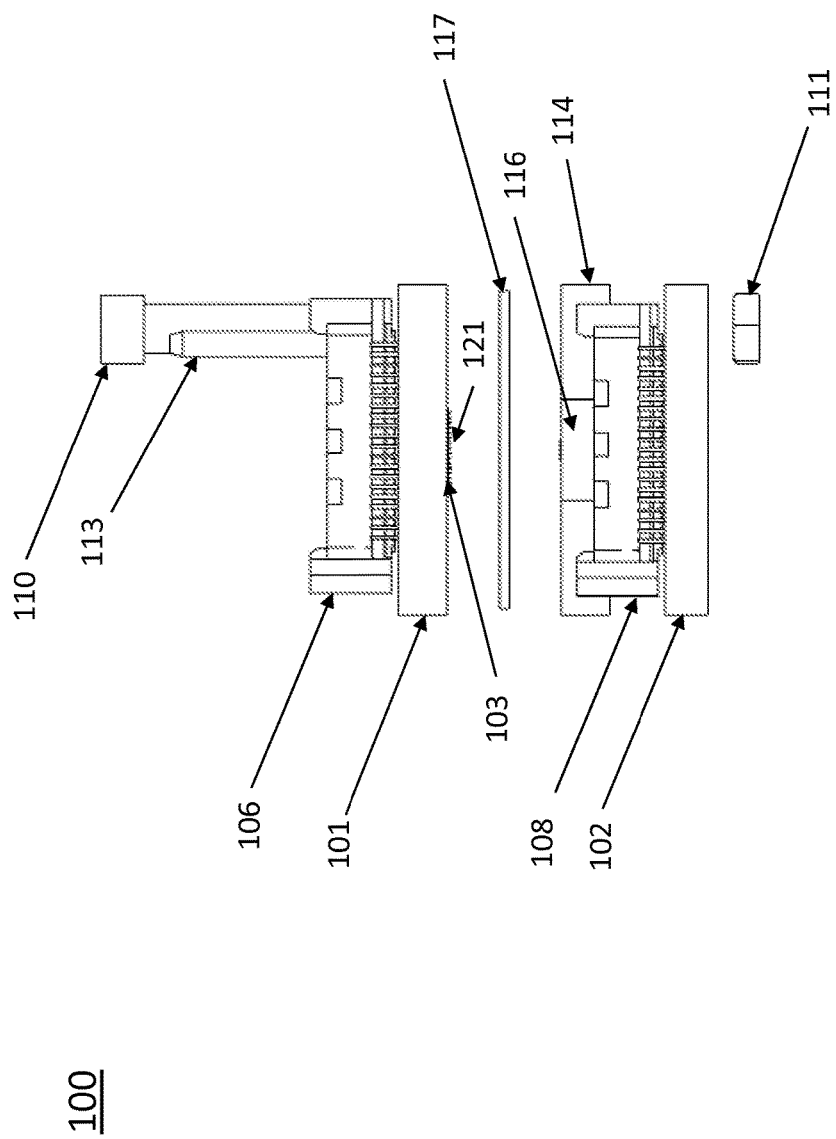
FIG. 2 illustrates a 2D backside view of a de-assembled embodiment of the disclosure using a neuroprobe.

FIG. 2 illustrates a backside view of an embodiment of a de-assembled stimulation device 100. Illustrated are: an electrical connector 106 and a probe 103 with grating couplers 121 located on a first support 101; an optical connector 108 located on a second support 102; an interface fitting 114 with cut-out 116; a gasket fitting 117; a nut 111; a bolt 110; and a guiding post 113.

Figure 3:
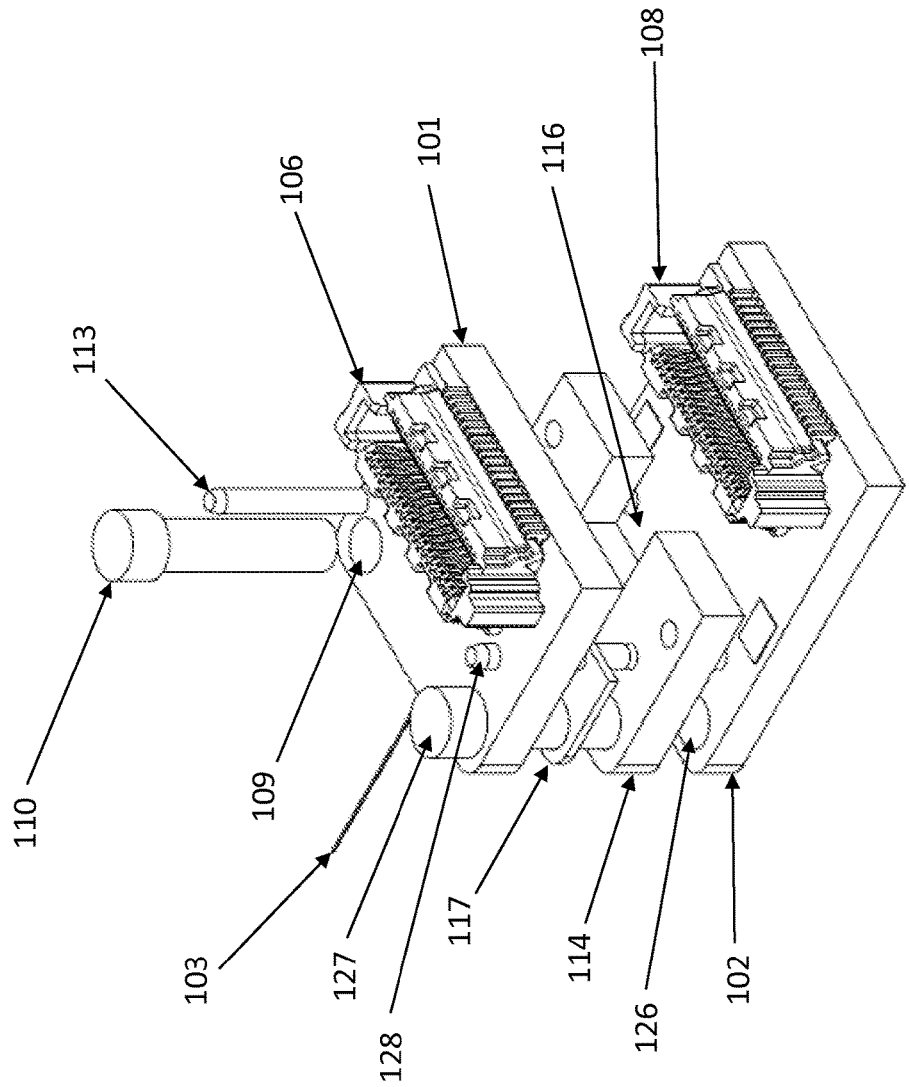
FIG. 3 illustrates a 3D frontside view of an embodiment of the disclosure using a neuroprobe.

FIG. 3 illustrates a 3D view of the backside of a de-assembled stimulation device 100. Illustrated are: an electrical connector 106 and a probe 103 located on a first support 101 with through-holes 109; an optical connector 108 located on a second support 102 with a trough-hole 126 suitable for receiving a bolt 110; an interface fitting 114 with a cut-out 116; a gasket fitting 117; two bolts 110, 127; and two guiding posts 113, 128.

Figure 4:
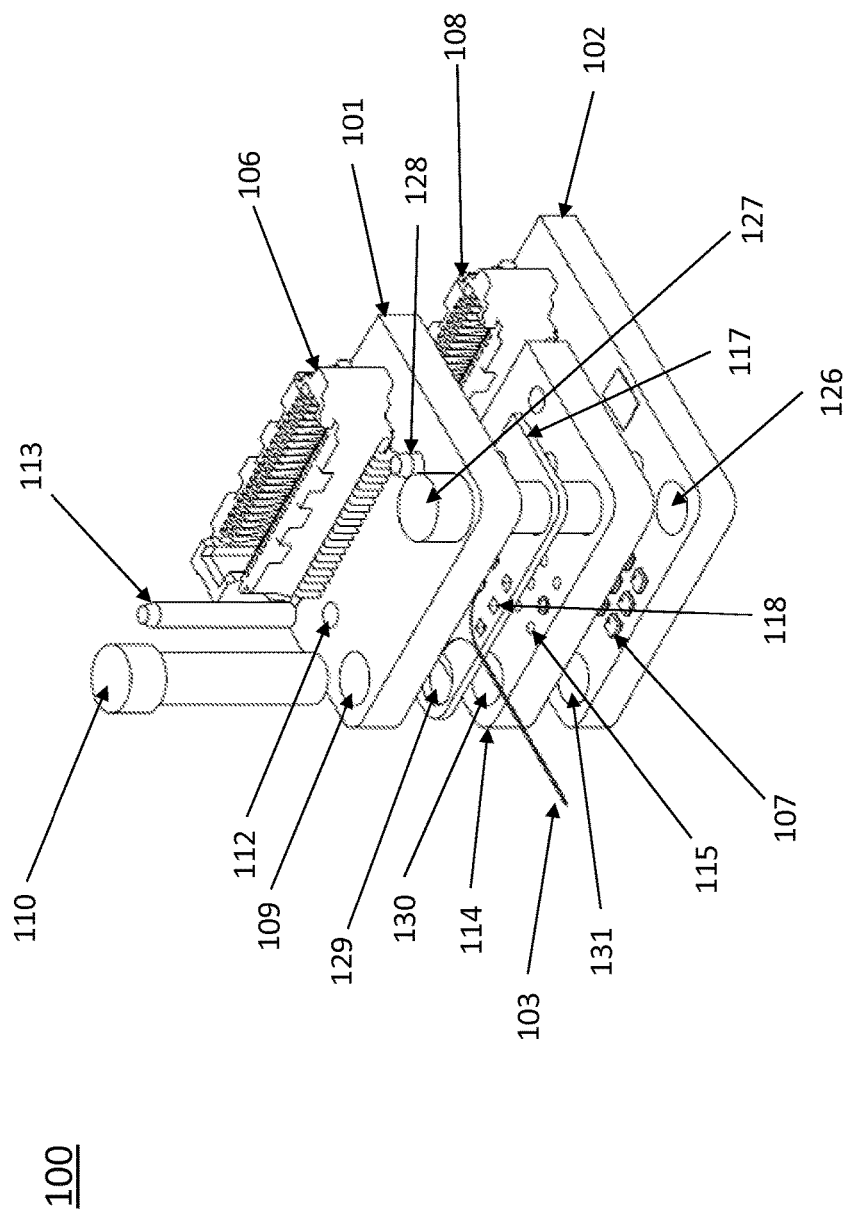
FIG. 4 illustrates a 3D frontside view of an embodiment of the disclosure using a neuroprobe.

FIG. 4 illustrates a 3D view of the frontside of a de-assembled stimulation device 100. Illustrated are: two bolts 110, 127; two guiding posts 113, 128; an electrical connector 106 and a probe 103 located on a first support 101 with through-holes 109; an optical connector 108 and optical sources 107 located on a second support 102 with through holes 126, 131; a gasket fitting 117 with through holes 118, 129; and an interface fitting 114 with through holes 115, 130.

The first support 101 comprises the probe 123, which is attached to a first side 104 of the first support 101. According to an embodiment of the disclosure, the probe 103 is glued to the first support 101. The probe 103 comprises grating couplers 121 that are facing away from the first side 104 of the first support 101. The grating couplers 121 are used to couple light from one or more optical sources 107 into the probe 103. The optical sources 107 are mounted onto the second support 102. According to an embodiment of the disclosure, the optical sources 107 may be LEDs. The first support 101 can be attached to the second support 102 by using a means for detachably attaching the first support 101 to the second support 102. According to an embodiment of the disclosure, the means for detachably attaching the first support 101 to the second support 102 may be a nut 111 and a bolt 110. When a nut 111 and a bolt 110 are used, the first and second support 101, 102 may feature a through-hole 109, 126, 131 allowing insertion of the bolt 110 through both supports 101, 102. Multiple through-holes 109, 126, 131 may be present if multiple nuts 111 and bolts 110 are used to attach both supports 101, 102 to each other.

Figure 10:
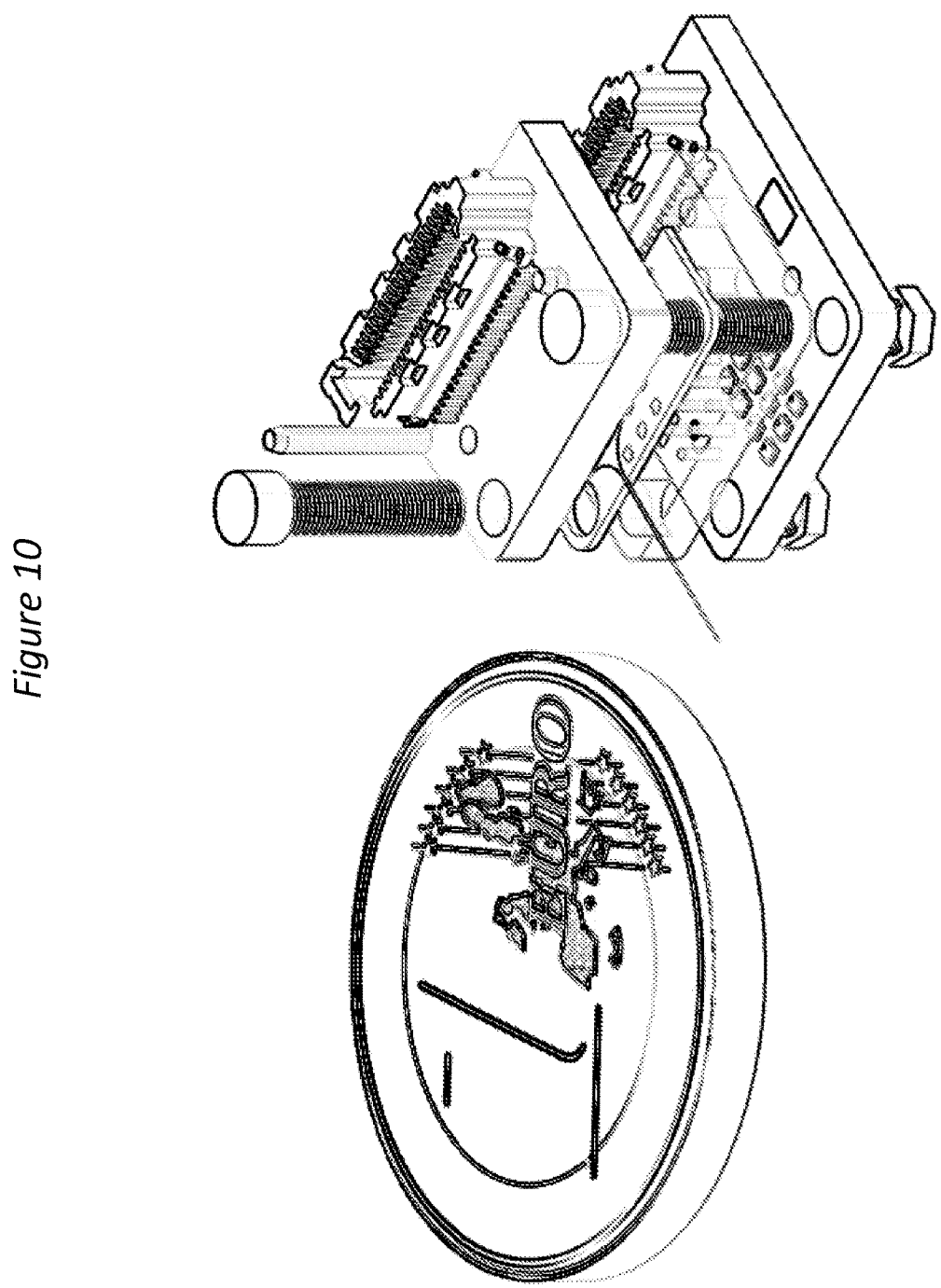
FIG. 10 illustrates the compactness of the device in accordance with an embodiment.

The first support 101 can be detached from the second support 102, which allows re-use of the second support 102 while the first support 101 can be disposed of. As a potential advantage, this reduces costs as expensive electronic parts (e.g., optical sources 107 on the second support 102) may be reused instead of being disposed of. This is in contrast with state of the art devices that cannot be de-assembled and therefore their reusability is limited. As the optical sources 107 are part of the stimulation device 100 no bulky optical fibers need to be attached to the device 100 for providing optical signals that may limit the compactness of the device. As a potential advantage, the device 100 may be very compact. FIG. 10 illustrates the compactness of the device 100 by comparing it with a one euro coin. Also, in contrast with the use of optical fibers, no care must be taken towards the angle of the optical signal entering the device as the optical sources 107 are fixed on the second support 102.

When the first support 101 is attached to the second support 102, the position of one optical source 107 is aligned with the position of one grating coupler 121. This allows light emitted by the optical source 107 to be received by the grating coupler 121 to which it is aligned. As a potential advantage, a more intense optical signal may be received by the grating coupler 121. When multiple optical sources 107 are present on the second support 102, each optical source 107 is associated with a different grating coupler 121 on the probe 103. In one example, one optical source 107 can only be associated with one grating coupler 121.

According to an embodiment of the disclosure, the first and/or second supports 101, 102 are printed circuit boards. The use of printed circuit boards allows the addition of other electronic components on both supports 101, 102 that may be electrically interconnected using wire bonding. According to an embodiment, a processor or other components may be mounted on the first support 101 enabling pre-processing of data sensed by electrodes on the probe 103, for example.

Figure 5:
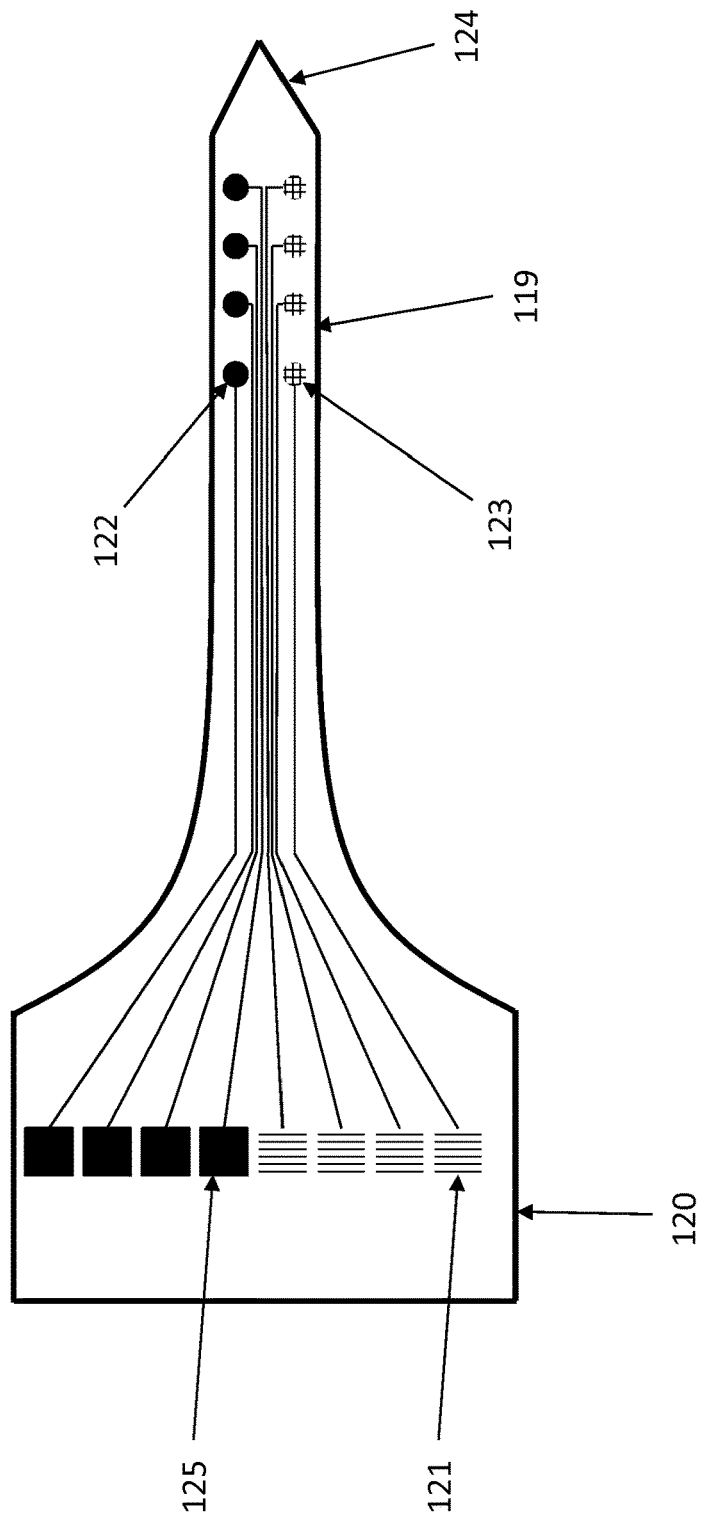
FIG. 5 illustrates an embodiment of a probe.
Figure 6:
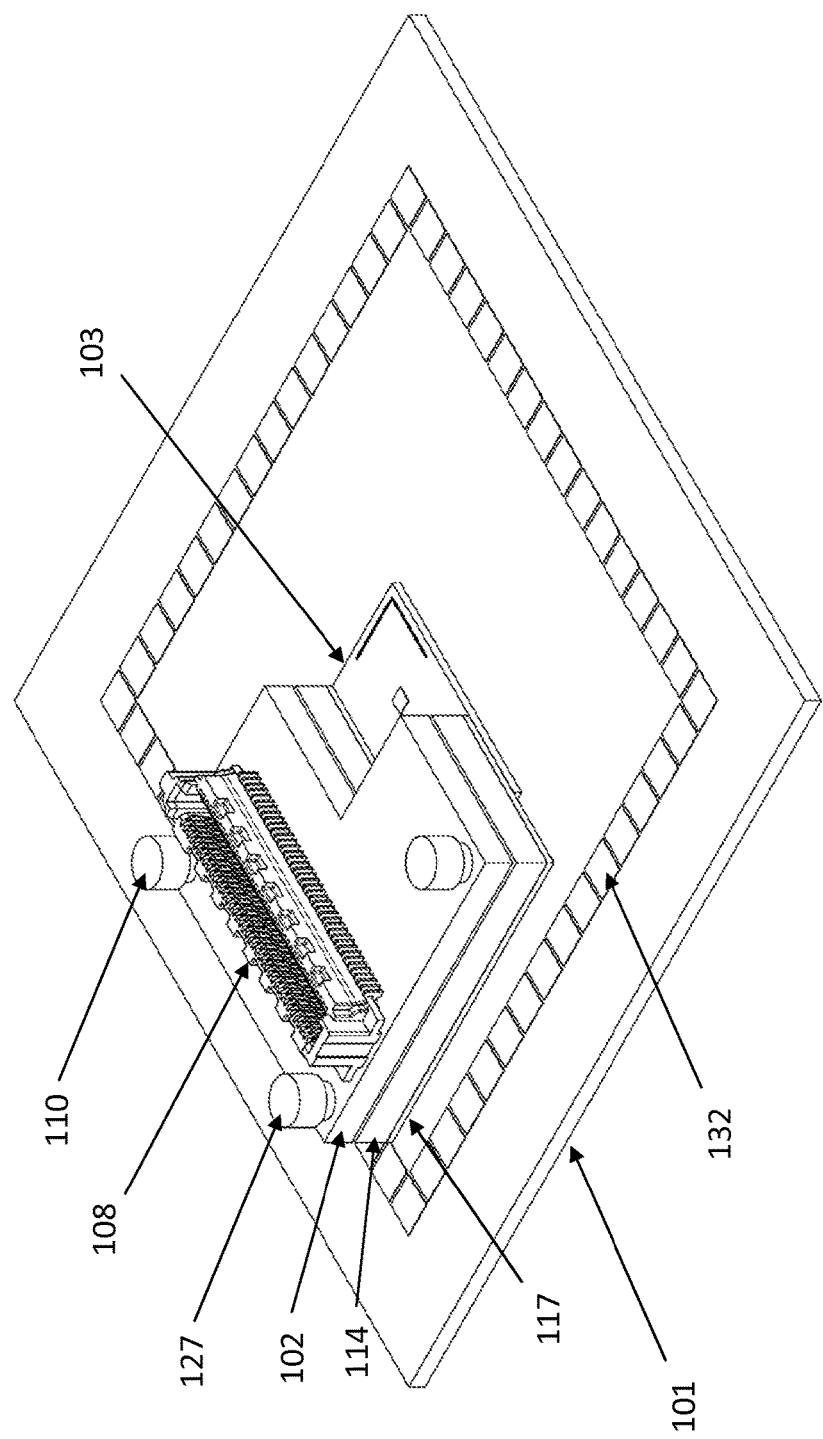
FIG. 6 illustrates a 3D frontside view of an embodiment of the disclosure using a micro-chip.
Figure 7:
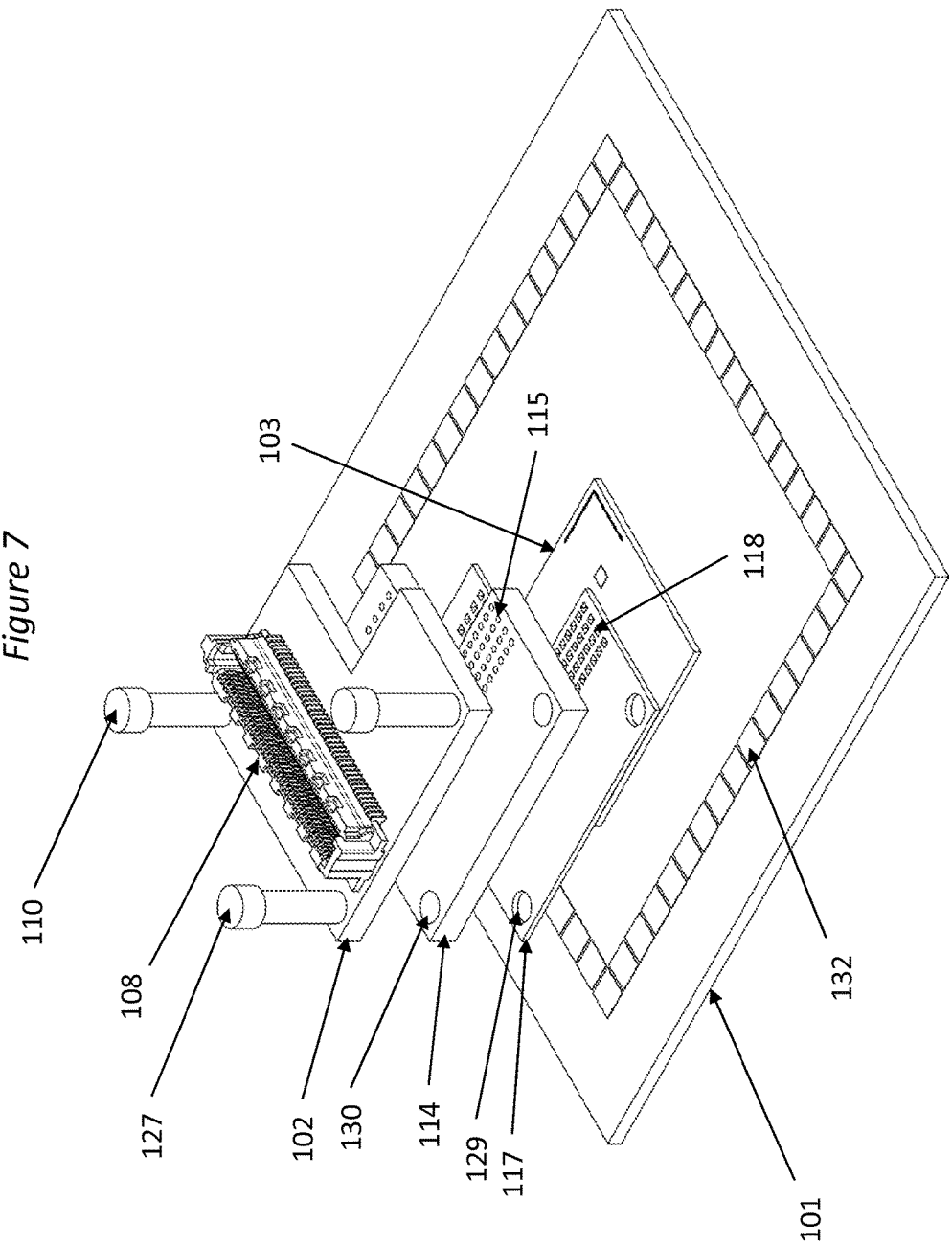
FIG. 7 illustrates a 3D frontside view of a de-assembled embodiment of the disclosure using a micro-chip.

According to an embodiment of the disclosure, the probe 103 further comprises a tip 124, a shaft 119 that includes at least one electrode 122, and at least one optical stimulation site 123. The optical stimulation site 123 may be optically connected to the at least one grating coupler 121. In this embodiment, the at least one grating coupler 121 is mounted on a head 120, the head 120 is mounted on the first support 101, and the head further comprises at least one bondpad 125 electrically connected to the at least one electrode 122. FIG. 5 illustrates an embodiment of a probe 103.

The probe 103 may be used as an in-vivo device wherein the shaft 119 of the probe 103 may be inserted in the human body or brain to stimulate tissue or cells.

The shaft 119 of the probe 103 may comprise one or more optical stimulation sites 123 that may be used to optically stimulate biological cells such as neurons. According to an embodiment of the disclosure, an optical waveguide may be embedded in the probe 103 connecting each stimulation site 123 optically to a different grating coupler 121. One or more grating couplers 121 are present on the head 120 of the probe 103. Additionally, the shaft 119 of the probe 103 may comprise one or more electrodes 122 (e.g., metal electrodes) that may be used to record biological signals from cells. The electrodes 122 are electrically connected to bondpads 125 located on the head of the probe via a metal wire that may be embedded in the probe 103.

The head 120 of the probe 103 is attached to the first support 101. This allows the shaft 119 to be inserted in the body or in the brain while the first support 101, the second support 102 and the head 120 remain external to the body or brain. As a potential advantage, the device may be used as an in-vivo device. To ease insertion, the tip 124 of the probe 103 may be a sharp tip.

According to an embodiment of the disclosure, the probe 103 may comprise a silicon substrate, an interconnection layer, at least one electrode 122 electrically connected to at least one bondpad 125 via the interconnection layer, and at least one optical stimulation site 123 optically connected to the at least one grating coupler 121 via the interconnection layer.

The probe may comprise a silicon substrate, atop the silicon substrate, an interconnection layer may be present, and atop the interconnection layer grating couplers, optical stimulation sites, and electrodes may be present. The interconnection layer may comprise electrical and optical connections and may function as an interconnection between electrical components and between optical components. The at least one grating coupler 121 may be optically connected to the at least one optical stimulation site 123 via an optical waveguide that may be part of the interconnection layer. The at least one bondpad 125 may be electrically connected to the at least one electrode 122 via metal wires that may be part of the interconnection layer. The probe 103 may be attached (e.g., glued) to the first support 101 such that the at least one electrode 122, the at least one grating coupler 121, and the at least one optical stimulation site 123 are facing away from the first support 101 to allow recording and stimulation of biological cells or slices of biological tissue placed or grown on the silicon chip. Such an embodiment is illustrated in FIGS. 6, 7, 8a, 8b, 9a and 9b. The probe 103 may be a micro-chip (e.g., a silicon chip). This extends the use of the device to in vitro applications. The device may be used to grow cells or place a tissue slice on the probe 103 and stimulate/record the cells or tissue slice.

According to an embodiment of the disclosure, the first support 101 further comprises an electrical connector 106 located on the first support 101 and electrically connected to the at least one bondpad 125 of the probe 103. The electrical connector 106 may be mounted on the first support 101. If the probe 103 is a micro-chip (e.g., a biosensor), the electrical connector 106 may be at least one external bondpad 132 that may be electrically connected to at least one bondpad 125 of the micro-chip via metal wires that may be embedded in the first support 101.

The electrical connector 106 may be used to connect an external registration device that receives, records, and/or processes signals from biological cells, sensed by electrodes present on the probe 103. The external registration device may be a computing unit. The electrical connector 106 may be electrically connected to bondpads 125 of the probe 103 via bond wires. The bondwires may be embedded in the first support 101. According to an embodiment of the disclosure, the electrical connector 106 is mounted on the side of the first support 101 opposite to the first side 104 of the first support 101. The location of the electrical connector 106 may be determined and changed to increase the compactness of the device 100.

According to an embodiment of the disclosure, the second support 102 further comprises an optical connector 108 electrically connected to the at least one optical source 107 for powering and/or controlling the at least one optical source 107.

The optical connector 108 may be electrically connected to the optical sources 107 via bond wires. The optical connector 108 may be used to power and/or to control the optical sources 107. The optical connector 108 may be connected to an external device suitable for generating the signals for driving and/or powering the optical sources 107, e.g., an electric signal generator. According to an embodiment of the disclosure, the optical connector 108 may be mounted on the first side 105 of the second support 102. The location of the optical connector 108 may be determined and changed to increase the compactness of the device 100, e.g., the optical connector 108 may be mounted on the side opposite to the first side 105 of the second support 102.

According to an embodiment of the disclosure, the first or the second support 101, 102 further comprises at least one guiding means 113, 128 for aligning the position of the at least one grating coupler 121 with the position of the at least one optical source 107.

According to an embodiment of the disclosure, the guiding means 113 include one or more posts that are positioned on the first or the second supports 101, 102. The posts may be fabricated from a sturdy material such as a metal. The guiding means 113 are used to ease aligning the position of the grating couplers 121 of the probe 103 with the position of the optical sources 107 of the second support 102. The guiding means 113 may be positioned on the second support 102 wherein the first support 101 features a corresponding through-hole 112 to allow inserting the guiding means through the through-hole 112. When guiding means 113 are used, the position of the guiding means 113 are determined to automatically align the position of the optical sources 107 with the position of the grating couplers 121 when the first support 101 is attached to the second support 102. Before attaching the first support 101 to the second support 102, the guiding means 113 are inserted through their corresponding through-holes 112. Thereafter, the first support 101 may be attached to the second support 102.

According to an embodiment of the disclosure, the stimulation device 100 further comprises an interface fitting 114 located in between the first support 101 and the second support 102. The interface fitting 114 comprises at least one through-hole 115 of which the position is aligned on one side of the interface fitting 114 with one of the at least one grating coupler 121, and on the other side of the interface fitting 114 with one of the at least one optical source 107.

The through holes 115 in the interface fitting 114 confine the light emitted by optical sources 107 resulting in an aligned optical signal being received by grating couplers 121. Also, cross illumination between different optical sources may be avoided. The interface fitting 114 helps to ensure that cross-illumination between optical sources 107 is avoided. As a potential advantage, multiple optical sources 107 may be used. Each grating coupler 121 is allowed to receive light from one corresponding optical source 107. To help to avoid light from other optical sources 107 different from its corresponding optical source 107 being received by a grating coupler 121, the interface fitting 114 is placed in between the first and the second support 101, 102. For each optical source 107 and its corresponding grating coupler 121, a through-hole 115 is present in the interface fitting 114. The position of the through-hole 115 corresponds on one side of the interface fitting 114 with a grating coupler 121, and on the opposite side with its corresponding optical source 107.

According to an embodiment of the disclosure, the interface fitting 114 may be a printed circuit board. According to another embodiment of the disclosure, the interface fitting 114 may be fabricated from a thermal insulating material (e.g., a thermal insulating polymer composite material). The thermal insulating material may be used to isolate the probe 103 from any heat that may be generated by optical sources 107. By using the interface fitting 114, a distance equal to the thickness of the interface fitting 114 is created between the first support 101 and the second support 102. As a potential advantage, the distance helps to ensure that heat that may be generated by the optical sources 107 is not transferred to the probe 103, which can help to minimize tissue damage in the brain caused by the heating up of the probe 103.

According to an embodiment of the disclosure, the interface fitting 114 features a cut-out 116 for providing space for bond wires on the first support 101.

The interface fitting 114 is positioned in between the first support 101 and the second support 102. The interface fitting 114 may feature a cut-out 116 or an opening to avoid bond wires that connect the electrical connector 106 to the probe 103 and that are present on the first side 104 of the first support 101, being covered or squeezed by the interface fitting 114. As a potential advantage, this allows the device to be more compact. The interface fitting 114 may further comprise other through-holes 130 to accommodate a means for attaching the first support 101 to the second 102 support and/or to accommodate a guiding means.

According to an embodiment of the disclosure, the stimulation device 100 further comprises a gasket fitting 117 located in between the first support 101 and the second support 102. The gasket fitting 117 comprises at least one through-hole 118 of which the position is aligned on one side of the gasket fitting 117 with one of the at least one grating coupler 121, and on the other side of the gasket fitting 117 with one the at least one optical source 107.

According to an embodiment of the disclosure, the gasket fitting 117 is fabricated from a flexible or elastic material. The gasket fitting 117 may be located in between the first support 101 and the interface fitting 114. As the gasket fitting 117 is flexible, it helps to ensure a good and tight fitting between the interface fitting 114 and the first support 101 when the first support 101 is attached to the second support 102. As a potential advantage, light from optical sources 107 is not diffused when reaching grating couplers 121. The gasket fitting 117 features through-holes 118 of which the number and position correspond to the number and position of through-holes 115 of the interface fitting 114. The gasket fitting 117 may further comprise other through-holes 129 to accommodate a means for attaching the first 101 to the second 102 support and/or to accommodate a guiding means.

The invention claimed is:

1. A partially implantable optical, neural stimulation device comprising:
   a first support including a processor;
   a second support, the first support and the second support configured to be placed outside a skull of a patient;
   a probe attached to the first support, the probe configured to be partially implanted in a brain of the patient, the probe comprising:
      an array of grating couplers for coupling optical stimulation signals into the probe;
      a silicon substrate;
      an interconnection layer atop the silicon substrate and under the array of grating couplers;
      at least one bondpad;
      at least one electrode electrically connected to the at least one bondpad via the interconnection layer; and
      an array of optical stimulation sites optically connected to the array of grating couplers via the interconnection layer, wherein the optical stimulation sites are arranged to stimulate particular neural areas;
   an array of optical sources for providing the optical stimulation signals, wherein the array of optical sources is mounted to the second support;
   an interface fitting made from thermally insulating material and located in between the first support and the second support,
   wherein the interface fitting comprises an array of through-holes aligned:
      on one side of the interface fitting with the array of grating couplers; and
      on another side of the interface fitting with the array of optical sources; and
   at least one means for detachably attaching the first support to the second support,
   wherein the first support is attached to the second support by the means for detachably attaching the first support to the second support.

2. The partially implantable optical, neural stimulation device according to claim 1, wherein the probe further comprises:
   a head mounted to the first support;
   a tip; and
   a shaft comprising:
      the at least one electrode that is electrically connected to the at least one bondpad via the interconnection layer; and
      the array of optical stimulation sites that is optically connected to the array of grating couplers,
   wherein the array of grating couplers is mounted to the head, and wherein the head comprises at least one bondpad electrically connected to the at least one electrode.

3. The partially implantable optical, neural stimulation device according to claim 1, further comprising an electrical connector connected to the at least one bondpad via bond wires, wherein the electrical connector is configured to provide signals from biological cells sensed by the at least one electrode to an external registration device that receives, records, and processes the signals.

4. The partially implantable optical, neural stimulation device according to claim 2, wherein the first support comprises an electrical connector that is electrically connected to the at least one bondpad.

5. The partially implantable optical, neural stimulation device according to claim 4, wherein the second support comprises an optical connector electrically connected to the array of optical sources for powering or controlling the array of optical sources.

6. The partially implantable optical, neural stimulation device according to claim 5, wherein the at least one means for detachably attaching the first support to the second support comprises a bolt and a nut.

7. The partially implantable optical, neural stimulation device according to claim 5, wherein at least one of the first support or the second support comprises at least one guiding means for aligning the array of grating couplers with the array of optical sources.

8. The partially implantable optical, neural stimulation device according to claim 5, wherein the interface fitting comprises a cut-out for providing space for bond wires on the first support.

9. The partially implantable optical, neural stimulation device according to claim 8, further comprising a gasket fitting located in between the first support and the second support, wherein the gasket fitting includes at least one through-hole aligned:
   on one side of the gasket fitting with one of the array of grating couplers; and
   on another side of the gasket fitting with one of the array of optical sources.

10. The partially implantable optical, neural stimulation device according to claim 9, wherein the probe is glued to the first support.

11. The partially implantable optical, neural stimulation device according to claim 10, wherein each of the first support, the second support, and the interface fitting is a printed circuit board.

12. The partially implantable optical, neural stimulation device according to claim 11, wherein the gasket fitting is fabricated from an elastic material.

13. The partially implantable optical, neural stimulation device according to claim 12, wherein the array of optical sources comprises a light-emitting diode (LED).

14. The partially implantable optical, neural stimulation device according to claim 1, wherein the processor is configured to pre-process data sensed by the at least one electrode.

15. The partially implantable optical, neural stimulation device according to claim 7,
   wherein the at least one guiding means comprises one or more posts,
   wherein the one or more posts are positioned on the first support or the second support, and wherein the one or more posts are fabricated from metal.

16. The partially implantable optical, neural stimulation device according to claim 5,
wherein the thermally insulating material comprises a thermally insulating polymer composite material, and
wherein the thermally insulating polymer composite material isolates the probe from heat generated by the array of optical sources.

* * * * *